United States Patent [19]

Edwards et al.

[11] Patent Number: 4,704,603
[45] Date of Patent: Nov. 3, 1987

[54] GLUE DETECTION SYSTEM

[75] Inventors: Neil K. Edwards, Cincinnati; Michael W. Gorden, Middletown, both of Ohio

[73] Assignee: Journey Electronics Corp., Monroe, Ohio

[21] Appl. No.: 855,872

[22] Filed: Apr. 24, 1986

[51] Int. Cl.⁴ ............................................. G08B 21/00
[52] U.S. Cl. .................................. 340/674; 250/562; 250/572; 356/237; 493/128; 340/540
[58] Field of Search ................. 340/674, 603, 540; 493/128; 156/64, 378; 250/562, 572, 578; 356/237, 445, 448, 256

[56] References Cited

U.S. PATENT DOCUMENTS

| | | | |
|---|---|---|---|
| 1,258,294 | 3/1918 | Wright et al. | 493/128 |
| 3,588,513 | 6/1971 | Akamatsu et al. | 250/562 |
| 4,215,939 | 8/1980 | Miller et al. | 250/572 |

Primary Examiner—Glen R. Swann, III
Attorney, Agent, or Firm—Biebel, French & Nauman

[57] ABSTRACT

A glue detecting system uses linear filament lamps and photodiodes mounted in the ends of nonreflective tubes to distinguish between diffuse and specular reflections from the surface of a moving article. Sensor photodetectors are positioned directly over the locations where glue beads are intended to be present; reference photodiodes observe the surface where no glue is intended. The spacing between certain photodiodes in the direction of movement of the article may be used to determine the velocity of the article, and the intensity of the reflections is used to determine the presence of glue in the desired areas, and the presence of unwanted glue in other areas; the duration of the specular reflections is used to determine the volume of glue present. An alarm circuit indicates an insufficient amount of glue in the desired areas or the presence of unwanted glue in undesired areas.

13 Claims, 15 Drawing Figures

GLUE DETECTION SYSTEM

BACKGROUND OF THE INVENTION

In the manufacture of corrugated boxes, or boxes fabricated from other paper materials, blank sheets of the material are cut to size on a cutting machine. Glue is then applied to the board upon exit from the cutting machine by means of a suitable glue dispenser, usually glue wheels or extrusion nozzles. The applied glue forms linear beads in prescribed positions and of predetermined lengths on the board.

The board exits the cutter at a speed sufficiently high that visual verification of the proper application of the glue is not possible. Errors in glue application frequently go undetected until many scrap boards are produced. Common errors include the application of too much or too little glue, glue application in the wrong areas of the board, and glue splatters which occur outside of the area intended to be glued.

SUMMARY OF THE INVENTION

The glue detection system of this invention provides an automatic, high speed method of inspection of the glue patterns produced on the boards, and alerts the operator of the cutting machine or marks the defective boards if glue is improperly applied.

The glue detection system includes a glue detection sensor head connected to electronic control circuitry which interprets the sensor signals and compares the sensed glue patterns with desired patterns. The control circuitry is programmed to recognize the desired patterns and to provide an alarm when undesired glue application is detected.

The sensor head is mounted near the glue applicator such that the glued board passes directly under the sensor. The beads of glue are detected photoelectrically by detectors which discriminate specular reflection of light from the slightly convex and shiny surface of the glue bead from the diffuse light reflection from the unglued surface of the board. This discrimination of specular from diffuse reflection of light is the principle by which the sensor detects the presence of glue on the surface of the boards.

The sensor head includes a self-contained light source in the form of a linear filament lamp positioned parallel to the axis of the glue beads. The light from the filament is reflected specularly from the shiny surface of the glue bead and forms a high intensity image of the lamp filament on a photodetector positioned directly above the part of the paper where glue is expected. The light which illuminates the board is reflected diffusely and low light intensity is sensed by a reference photodetector positioned over the board where glue is not expected. The photodetectors are mounted at the end of nonreflecting tubes which serve to collimate the light reaching the detectors. This controls the field of view of each sensor since the sensors view a very small and well defined region of the board.

The sensor head also includes photodetectors placed over areas of the paper where no glue is to be applied in order to detect the presence of unwanted glue.

The photodetectors can also detect the presence or absense of boards as well as its speed. By detecting the passage of the leading or trailing edges of the board with photodetectors spaced apart by a known distance, the speed of the board through glue detector can be calculated and from this the control electronics can determine the position of the detected glue beads on the board and compare this result with the desired position as programmed by the operator.

It is generally acceptable to have skips or flaws in the applied glue bead, provided that an adequate total amount of glue has been applied. The control logic is programmable to allow a preset percentage of glue applied to be interpreted as good even though skips or missing traces occur.

It is therefore an object of this invention to provide an improved glue detecting device where the amount of glue in a desired area and the presence of glue in unwanted areas can be accurately and quickly ascertained.

It is also an object of this invention to provide a glue detecting device using the specular reflections of a light source to indicate the presence of glue beads on the surface of an article.

It is a still further object of this invention to provide an apparatus for detecting the presence of specular reflective substances on the surface of an article by comparing the intensity of the light reflected therefrom to the diffuse reflections from the surface of the article.

It is a further object of this invention to provide a method for detecting the presence of substances on preselected areas of a surface comprising the steps of: positioning sensor photodetector means for observing light reflected from the surface in the predetermined area; positioning reference photodetector means to observe areas which are intended to be free of the substance; providing light source means to illuminate preselected area whereby diffuse light reflected from the surface will be detected by each photodetector means in the absence of the substance and specular reflections will be observed when the substance is present in the field of view of either photodetector means; averaging the value of the light detected by the reference photodetector means; comparing the value of the light detected by said sensor photodetector means to said average value; and providing an output indicating the presence of the substance when the light value detected by the sensor photodetector means exceeds said average value by a predetermined amount.

It is another object of this invention to provide an apparatus for determining whether the surface of articles, such as blanks, have had glue properly applied thereto, said apparatus including first detecting means for sensing the presence of glue within a predetermined band on each article, second detecting means for sensing the presence of glue in a defined area adjacent said predetermined area, first circuit means responsive to said first detecting means for providing an output representing the presence of glue within said predetermined area, second circuit means responsive to said second detecting means for providing output representing the presence of glue in said adjacent area, and alarm circuit means for providing an alarm signal indicating an improperly glue surface whenever glue within said predetermined area deviates from a predetermined amount or whenever glue in excess of a second predetermined amount is present in said adjacent area.

Other objects and advantages of the invention will be apparent from the following description, the accompanying drawings and the appended claims

DESCRIPTION OF THE PREFERRED EMBODIMENT

Figure 1:
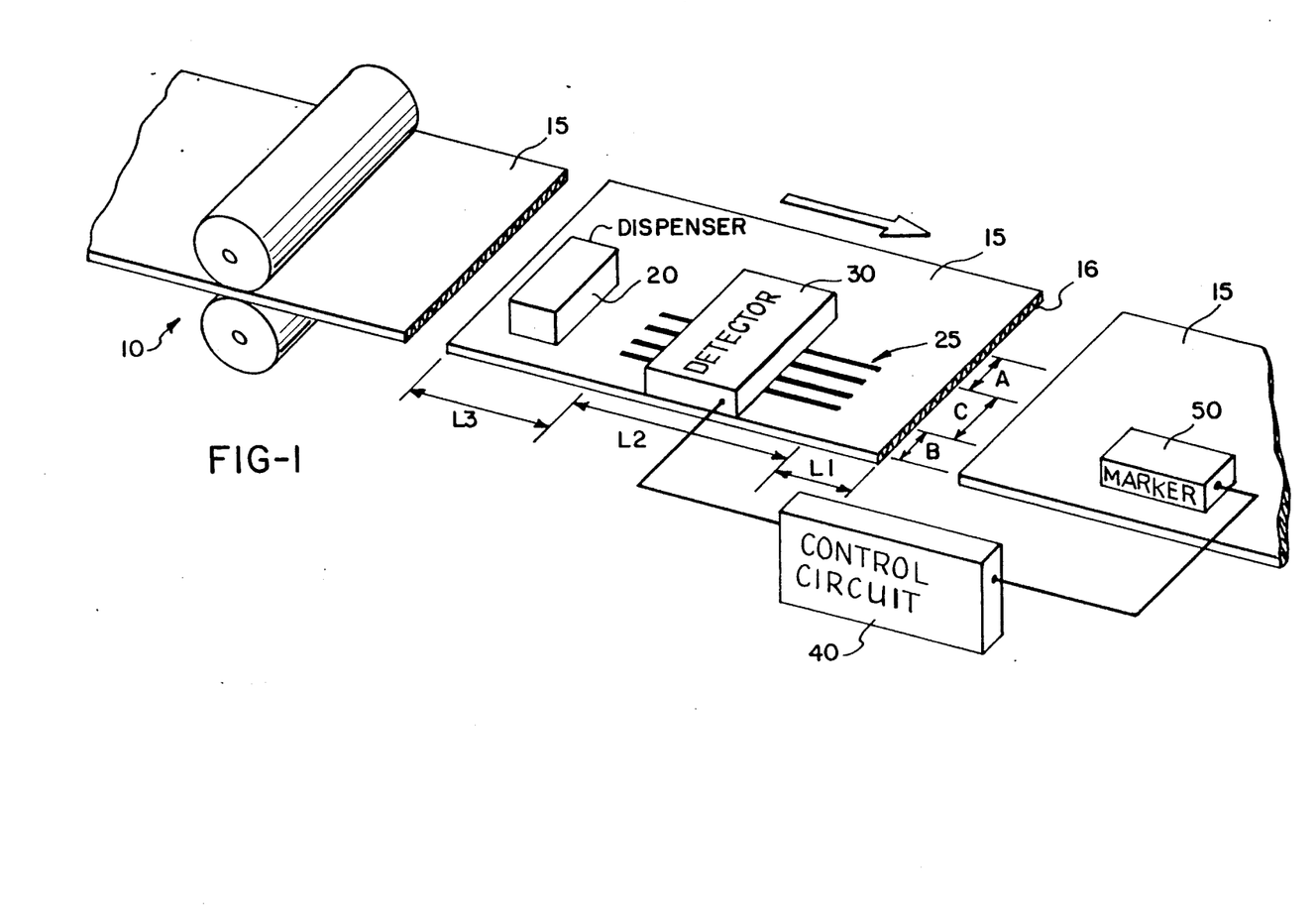
FIG. 1 is a schematic illustration showing the relationship between a board cutting and scoring machine, glue dispenser and the glue detector, control circuits and alarm device or marker.

Referring now to drawings which illustrate a preferred embodiment of the invention, and particularly to FIG. 1 which is a schematic illustration of one type of apparatus on which the present invention may be used, a board cutting and scoring machine, shown generally at 10, cuts sheets of material, such as cardboard, into blanks of predetermined sizes. The machine may also score the cardboard so it may be folded at preselected locations. As the boards exit the cutting and scoring machine 10, glue is applied thereto at predetermined locations and of predetermined lengths by a suitable glue dispensing mechanism 20. The glue dispenser 20 may be of any suitable type, usually employing glue wheels or extrusion nozzles. The glue forms linear beads on the surface of the boards.

A typical cardboard blank 15 is shown in FIG. 1 and may, for example, include four glue beads 25 in a glue zone C. No glue should be found on either side in zones A or B. Further, the glue in zone C should begin a distance L1 from the leading edge 16 of the blank and extend for not more than distance L2. No glue should be found in zone C before or after the designated area.

In the present invention, a glue detecting means or sensor head, shown generally at 30, is positioned to sense the presence of glue in zones A, B and C. Control circuit means 40 interprets the signals from the sensors in detecting means 30, and if any undesirable glue patterns are present, that is, if glue is detected outside of the desired areas, or if insufficient glue is deposited, then the boards may be appropriately marked or an alarm signal provided by the mechanism shown generally at 50.

Figure 2:
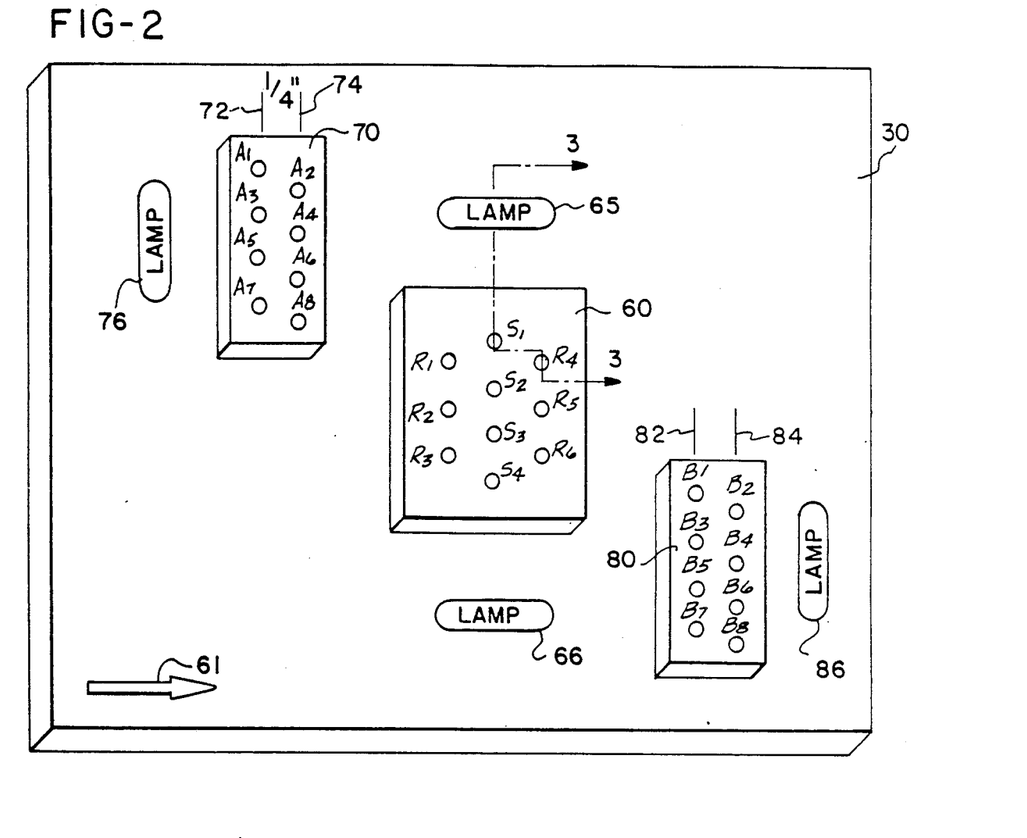
FIG. 2 is a plan view showing the locations of the photodetectors and light sources used in the glue detecting head assmbly.

The sensor head 30 preferably includes three separate photodetector housings as shown in FIG. 2. Housing 60 contains both sensor photodetectors S1-S4 and reference photodetectors R1-R6. The bead sensing photodetectors S1-S4 are aligned transverse to the direction of movement of the board 15, as represented by the arrow 61. The reference photodetectors R1-R6 are arranged in two groups on center lines on either side of the sensor photodetectors. The spacing between the bead sensing photodetectors is determined by the placement of the glue beads on the board. The reference photodetectors are placed between the glue beads to observe the board where no glue is expected to be present. The housing 60 includes a plurality of cylindrical openings 62 (FIG. 3), the axis of each being perpendicular to the plane of the board 15, with each opening controlling the field of view of the photodetector mounted at the rear thereof. The openings 62 thus form nonreflecting tubes to control the field of view of each photodetector.

Mounted adjacent the housing 60 are linear filament lamps 65, 66 for illuminating the board 15, particularly in the area directly beneath the photodetectors. The filaments of these lamps are aligned parallel to the glue beads 20. These lamps may be type 211-2, manufactured by General Electric Co.

Referring again to FIG. 2, the sensor head 30 includes a second photodetector housing 70 provided with openings to hold eight photodetectors A1-A8. The odd-numbered photodetectors are mounted in a straight line 72 oriented perpendicular to the movement of the board 15 on approximately one-quarter inch centers. The even-numbered photodetectors are also evenly spaced and offset from the odd-numbered photodetectors by approximately one-eighth inch on parallel center line 74. A linear filament lamp 75 illuminates the surface of the board directly beneath the housing 70 in zone A with its filament parallel to center lines 72 and 74.

A third photodetector housing 80 is also provided with openings to hold photodetectors B1-B8. The odd-numbered photodetectors are evenly spaced on one quarter inch centers along line 82, and the even-numbered photodetectors are also evenly spaced on center line 84, as shown in FIG. 2. Lamp 85 is arranged with its filament parallel to the center lines 82 and 84 and illuminates the area in zone B directly beneath the photodetectors.

Figure 3:
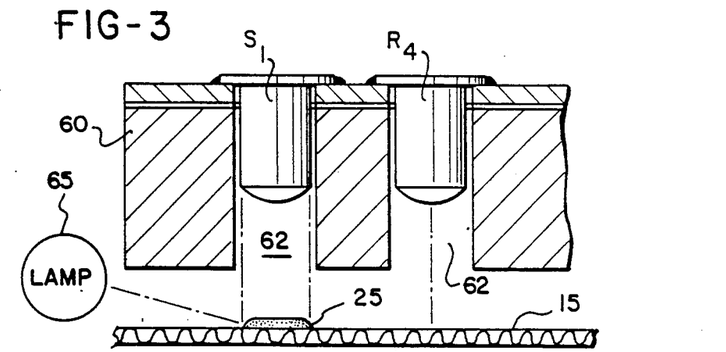
FIG. 3 is a cross sectional view taken along line 3—3 in FIG. 2 and shows the position of the photodetectors within a housing.

Referring to FIG. 3, if no glue is present, only diffuse light from the surface of the board 15 will be detected by the photodetectors. On the other hand, if glue is present on the board, or some other convex shiny substance is on the surface, light from the filament of the lamp will be reflected specularly. In FIG. 3, photodetector S1 is shown receiving light reflected specularly from glue bead 20 while reference photodetector R4 receives only diffuse reflections. The specular reflection is of a significantly higher intensity than diffuse reflections, and therefore the presence of a glue bead is easily detected.

The intensity of reflections off a surface, especially cardboard, can vary greatly, and because of this, it is necessary to compare the signals from the bead sensing photodetectors to a reference that truly represents the average diffuse reflection from the board at any given time.

Specular reflections are created because the glue bead is both shiny and has a curved or convex surface. As long as the sensor photodetector can view the specular reflection of the light source off of the curved surface, then the presence of glue will be indicated. If the glue bead is not viewable beneath the sensor photodetector, then, of course, the specular reflection will not be observed. If the glue bead appears beneath the photodetectors in zones A or B, then the presence of glue in an unwanted area will be detected, and that fact will generate an alarm indication.

As shown in FIG. 3, the area on the board viewed by the reference photodetector does not overlap the area observed by the sensor photodetectors, otherwise, the reference photodetectors would also see or sense the specular reflections from glue beads when they are in the proper location.

Figure 4:
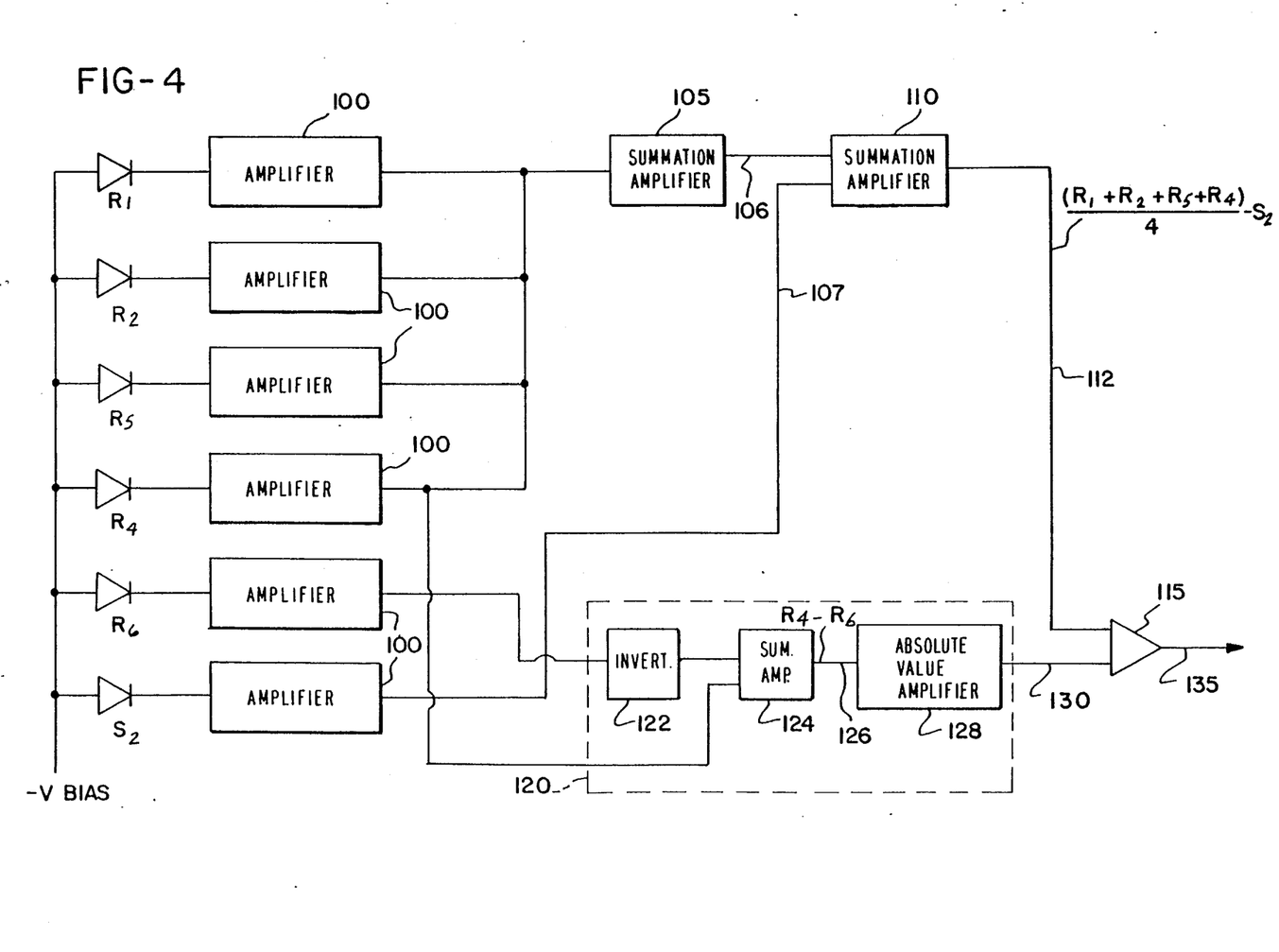
FIG. 4 is a simplified block diagram of the circuit for comparing a weighted average of diffusely reflected light to the intensity of the light from a bead sensing photodetector.

FIG. 4 is an electrical schematic diagram, in simplified form, illustrating the technique of taking a weighted average of the signals derived from the reference photodiodes, and comparing that average to the signal obtained from the sensor photodiode.

Reference photodiodes R1, R2, R4 and R5 surround sensor photodiode S2, as shown in FIG. 2. Each of the photodiodes is connected to a common bus labeled —V Bias. Each photodiode is also connected to a buffer amplifier 100. The outputs of the buffer amplifiers connected to reference photodiodes are sent to a summation amplifier 105, the output of which, on line 106 is a weighted average of the four reference photodiodes. The outputs of amplifier 105 and the output of the sensor photodiode S2 on line 107 are applied to a second summation amplifier 110 whose output on line 112 is the difference therebetween. This difference signal is applied to one input of comparator 115.

The outputs from photodiodes R4 and R6, representing the diffuse noise value, are used by the circuit 120 shown generally at the lower portion of FIG. 4. The output of photodiode R6, for example, is sent through an inverter 122 whose output is combined with the output of photodiode R4 in summation amplifier 124. The difference signal (R4–R6) on line 126 is applied to an absolute value amplifier 128, and its output 130 is filtered and applied to the other input of comparator 115.

Figure 5:
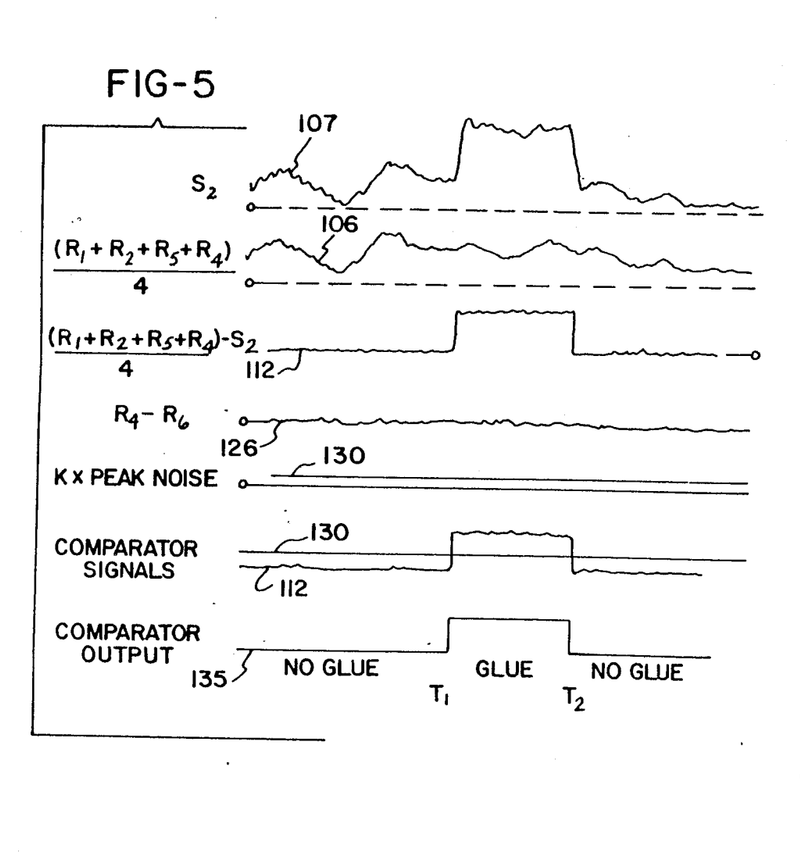
FIG. 5 is a set of electrical waveforms illustrating the signals at various locations in FIG. 4.

The waveforms at various points within the schematic diagram of FIG. 4 are illustrated in the waveforms of FIG. 5.

All of the photodiodes will sense diffused light deflected from the surface of the blank in the absence of glue or some other highly reflective curved substance. For cardboard blanks, the amount of diffused light received by the photodiodes can vary widely due to the composition, changes in color, reflectivity of the board or changes in the light output of the lamps, etc. Thus, as shown in FIG. 5, the light energy sensed by the photodiodes can vary widely as the blank passes the sensor head as shown by the signal on line 106. The circuit of FIG. 4, however, compensates for these changes in the light energy perceived by the photodiodes by taking the difference between what is observed by the reference on line 106 and sensor photodiode output on line 107. The result is that shown in the third waveform on line 112.

The fourth waveform illustrates the difference in outputs from two of the reference photodiodes (R4–R6) on line 126. Both of the photodiodes are assumed to be observing uncontaminated surface areas. This represents the diffusion noise signal and the peak value of this signal on line 130 is shown in the fifth waveforms. The magnitude of the signal on line 130 is therefore a floating reference against which the compensated signal on line 112 is measured. The absolute magnitude of the output, representing the difference between the sensor and the weighted reference signals on line 112, must exceed the noise value on line 130 before there is an indication that glue or some other reflective substance is present on the board beneath the sensor photodiode. Thus, in the illustration shown, the comparator 115 will provide an output on line 135 indicating the presence or absence of glue.

Figure 6:
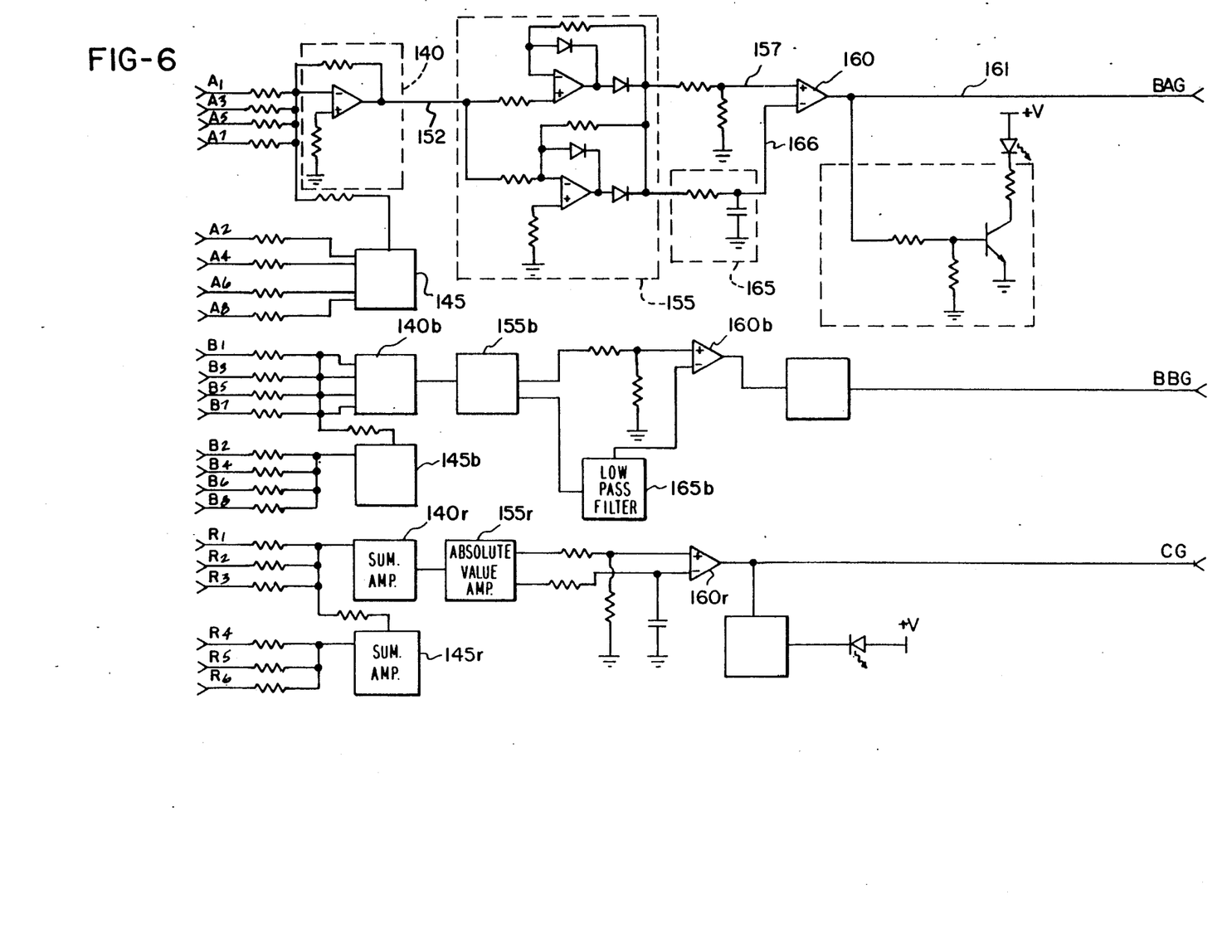
FIG. 6 is a simplified electrical schematic diagram of a circuit connected to the photodetectors monitoring the adjacent zones for indicating the presence of unwanted glue.

FIG. 6 is an electrical schematic diagram of the circuit sensing the outputs from each of the photodiodes in the border monitoring areas, zones A and B of FIG. 1. These are the areas where no glue is expected to be present, but if glue is detected, an alarm is to be provided. In FIG. 6, only the photodiodes A1–A8 in housing 70 will be discussed, but it is to be understood that the circuits for photodiodes B1–B8 in housing 80 and the reference photodiodes in housing 60 will operate in a similar manner. The odd numbered photodiodes are connected to a first summation amplifier 140, and the even numbered photodiodes are connected to a second summation amplifier 145. The output of summation amplifier 145 is connected to the first summation amplifier 140 as shown, and therefore, the voltage on line 152 represents the difference between the combined outputs of the even and the odd numbered photodiodes. This output is then applied through an absolute value amplifier 155 which provides a signal which is applied both directly on line 157 to a comparator circuit 160 and via line 166 through a low pass filter 165.

The low pass filter 165 serves to set the threshold of the comparator 160 and essentially detects the peak value of the noise from the photo detectors. Only if the difference signal changes rapidly and exceeds the noise value will an output be produced by the comparator 160 indicating that glue has been detected in the border area.

Figure 7:
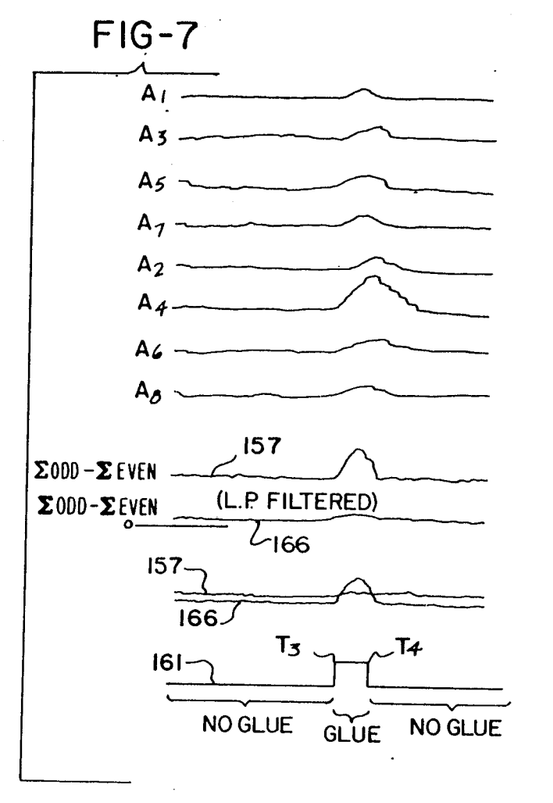
FIG. 7 is a set of waveform diagrams illustrating the electrical signals at various locations within the schematic FIG. 6.

The waveform diagrams of FIG. 7 illustrate the outputs of each of the photodiodes A1–A8. At time T3, for example, glue is detected by a photodiode A4, and its output increases substantially. The difference between the weighted average of the even numbered photodiodes, as compared to the odd numbered photodiodes, is represented as the input to the absolute value amplifier 155 and as one input to the comparator circuit 160. The filtered value on line 166 sets the threshold for the comparator circuit 160, and since the difference signal exceeds the threshold during the interval T3 and T4, the comparator provides an output indicating that glue is present only during that interval.

Figure 8:
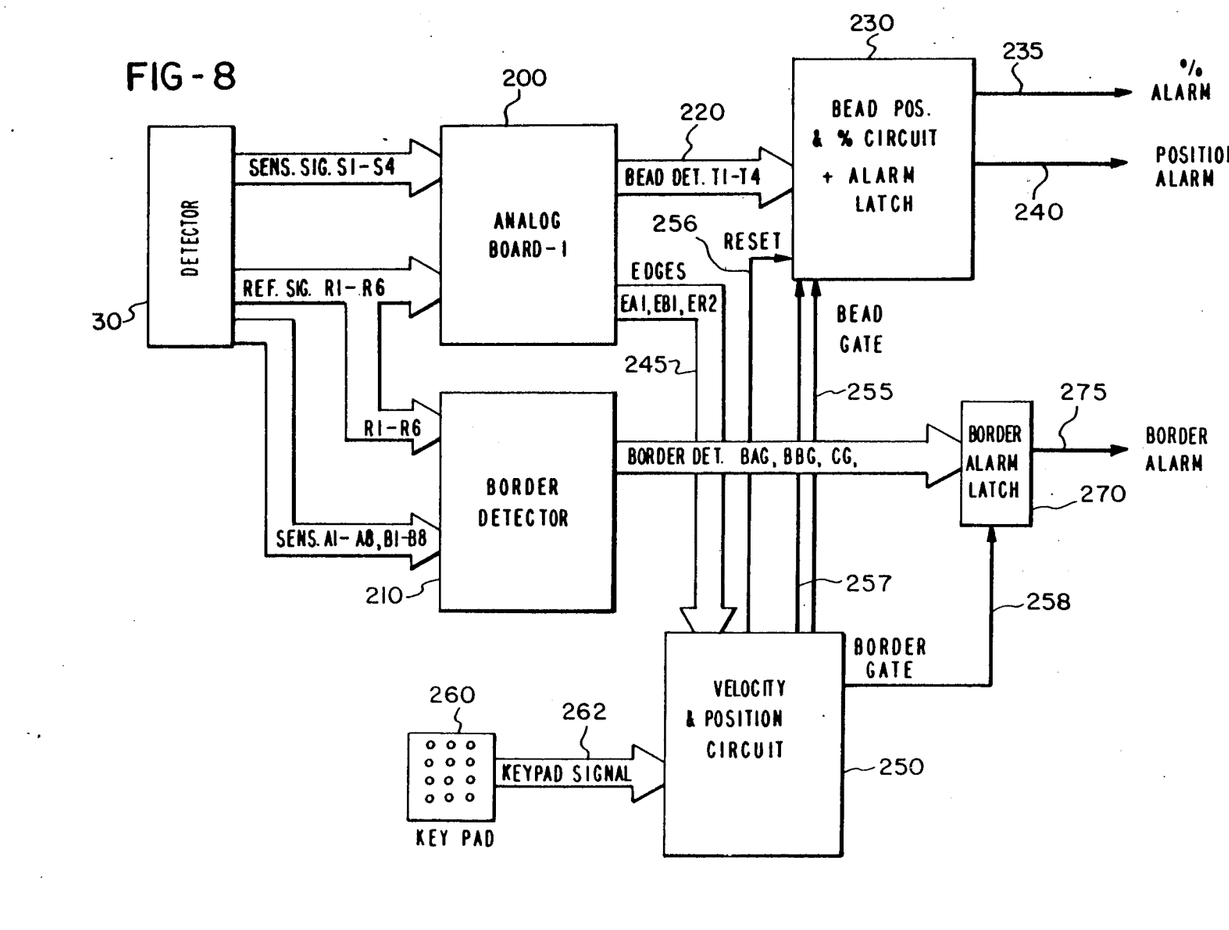
FIG. 8 is a electrical block diagram of the various major components included within this invention.

Referring now to the block diagram of FIG. 8, the detector or sensor assembly 30 provides the signals from the photodetectors that are used by the analog board 200 (FIGS. 4 and 10) and border detector board 210.

The analog board 200 processes the signals from the bead sensing photodetectors and the reference photodetectors and provides an output 220 to the circuit shown generally at 230 which identifies the location of the glue beads and the amount of glue contained therein. If the amount of glue is insufficient, an alarm is provided on line 235, and if the glue beads are in the incorrect position, an alarm indication is provided on line 240.

The circuit 200 also provides signals on line 245 to a velocity and position indicating circuit 250. The operator may use a keypad 260 to provide the system with information regarding lengths L1 and L2 (FIG. 1) and, in turn, the circuit 250 provides a bead gate signal on line 255, a reset signal on line 256 and an alarm strobe signal on line 257 to circuit 230, and a border gate signal on line 258 to a border alarm latch circuit 270.

The output of the border alarm latch circuit on line 275 activates an audio/visual alarm to alert the operator that glue has been sensed in the border area. The signal may additionally be used to activate the marking system 50 which identifies the detective board.

Figure 9:
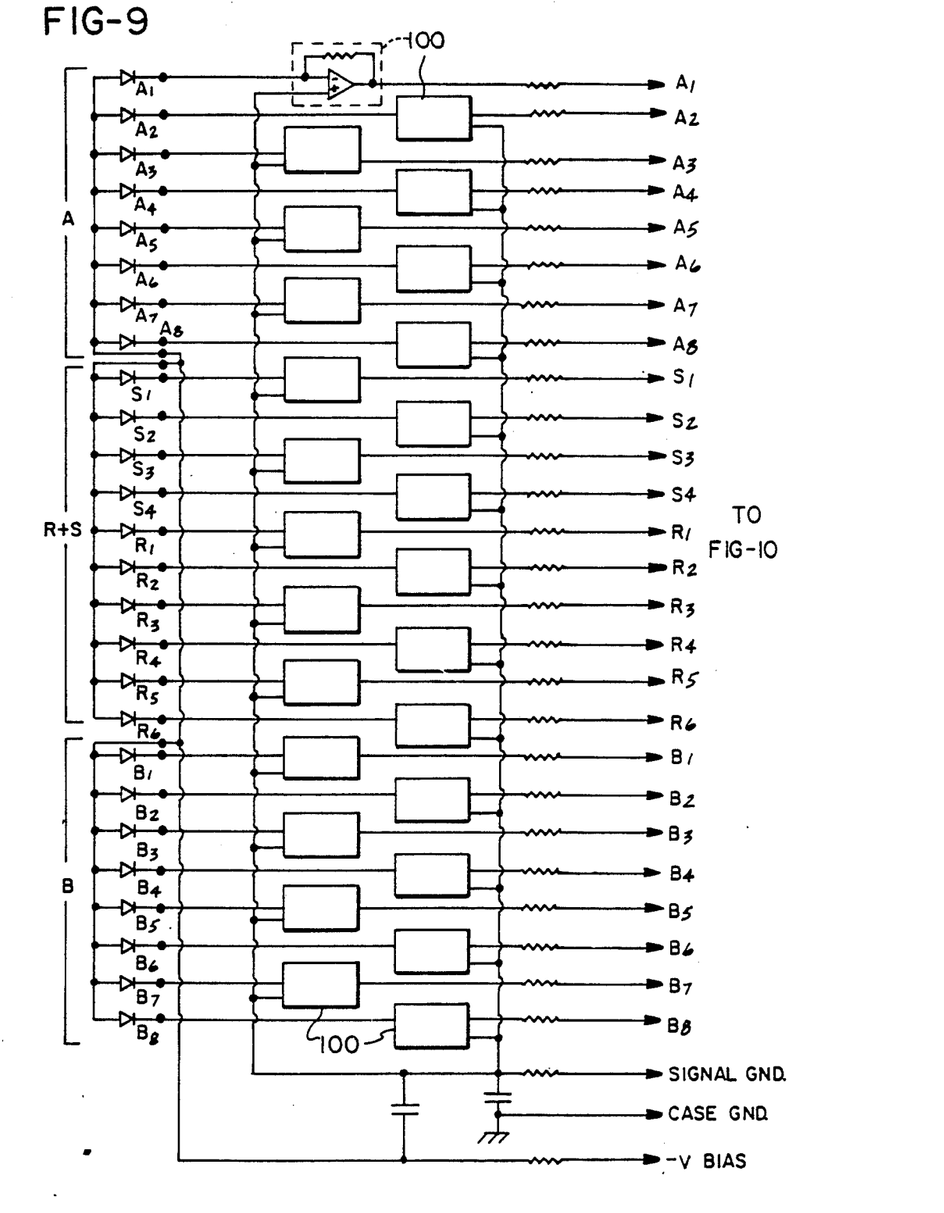
FIG. 9 is an electrical diagram showing the circuitry contained within the sensor head.

Turning now to the electrical schematic of FIG. 9, each of the photodiodes is connected through a buffer amplifier to their respective output terminals. As shown in FIG. 8, photodiodes S1-S4 are connected to the circuit 200. The reference photodiodes R1-R6 are connected to both circuits 200 and 210. The photodiodes A1-A8 and B1-B8 monitoring the border areas are connected to the border detector 210.

Figure 10:
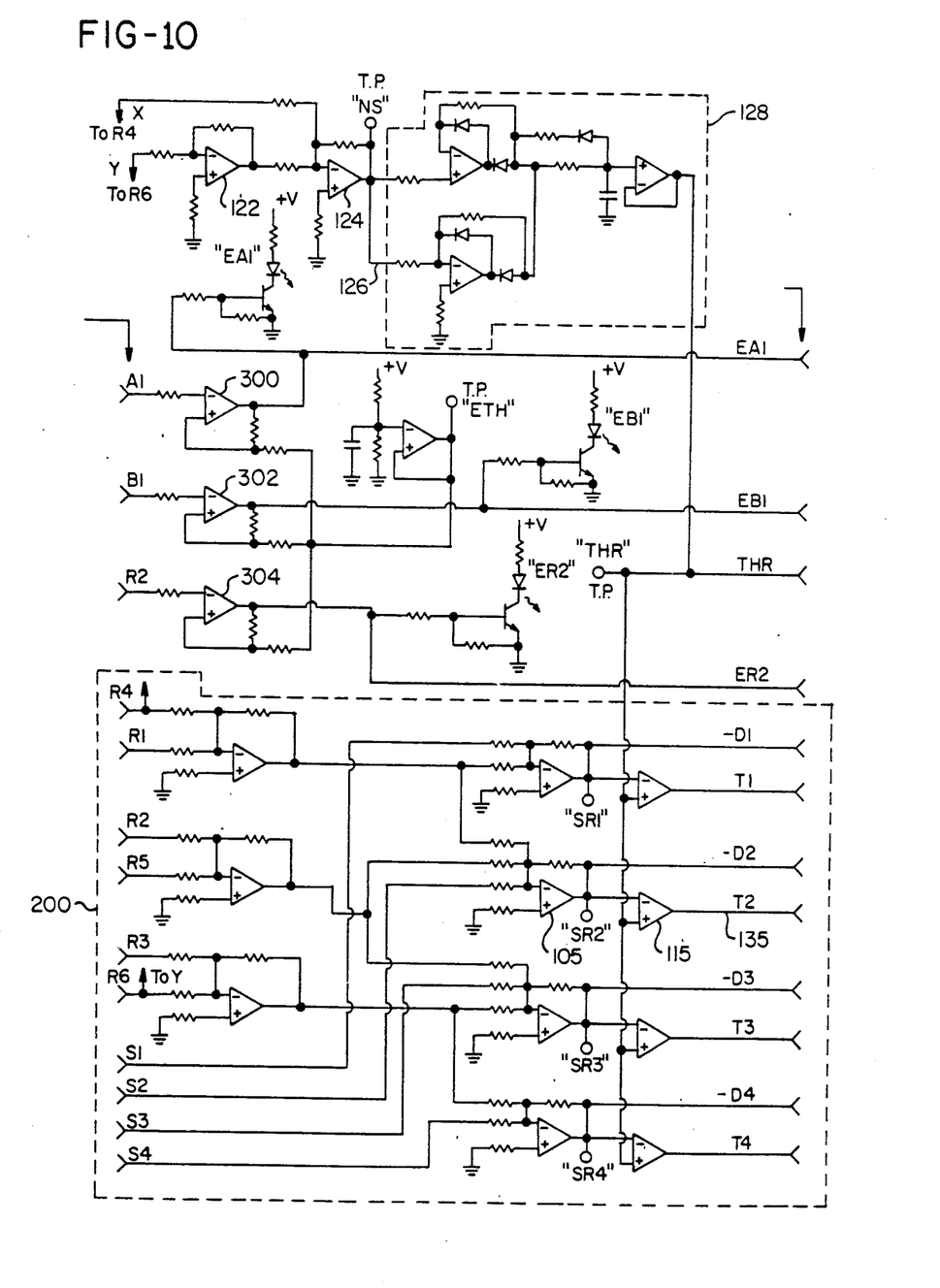
FIG. 10 is an electrical schematic diagram of a portion of the circuitry contained within the control circuit.
Figure 13:
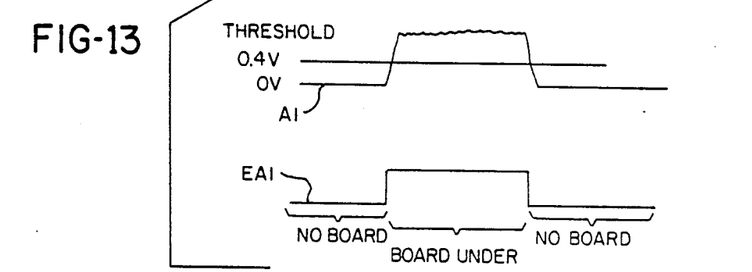
FIG. 13 is a waveform diagram showing signals in the edge detection circuitry of FIG. 10.

Referring now to FIG. 10, the photodiode connections are shown at the left, and the output signals from this circuit are shown at the right. Terminals EA1 and ER2 provide signals identifying the leading and trailing edges of each board as it passes beneath the detector. Photodiode A1 is connected to comparator circuit 300, the other input of which is a fixed value. Whenever a board passes beneath the photodetector, an output indicating that fact will appear on line EA1, as shown in FIG. 13. Similarly, photodiode B1 is connected through comparator 302, and provides an output on line EB1; photodiode R2 is connected through comparator 304 to provide an output on the line identified as ER2.

As shown in FIG. 13, the voltage output of photodiode A1 is shown near zero volts when no board is present since there is nothing to reflect any light by either diffuse or specular reflection into a photodiode. When a board passes under the photodiode, however, diffused light from a linear filament lamp will cause the voltage output of that photodiode to rise. A fixed threshold is used since the change in light intensity is significant and predictable. Thus, the output on line EA1 clearly shows when the board is or is not present beneath that particular photodetector.

The reference photodiodes and the sensor photodiodes are connected to the circuits shown generally at 200. A simplified version of this circuit was described in connection with FIG. 4. The outputs generated by this circuit are identified as T1 through T4.

Figure 11:
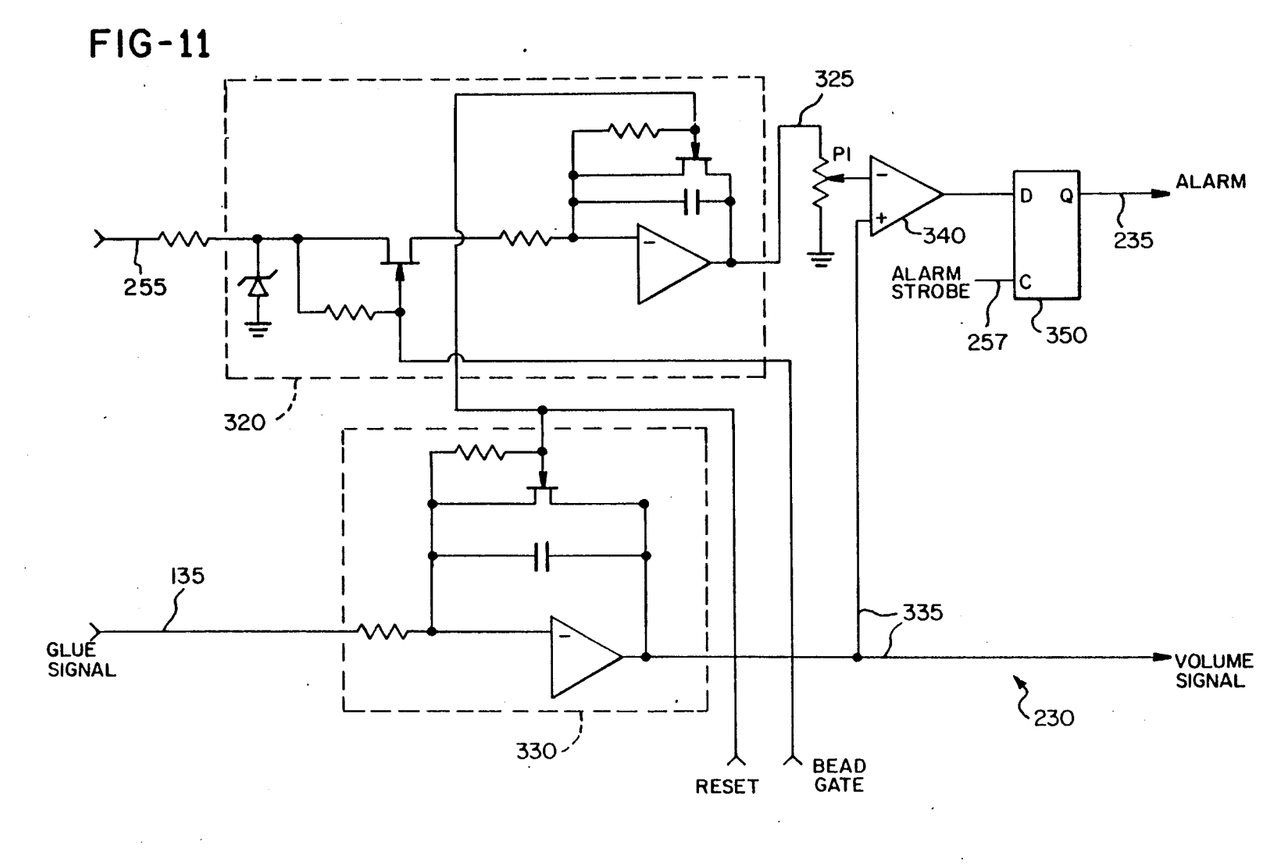
FIG. 11 is a electrical schematic diagram of the circuit for monitoring the amount of glue present in the desired glue zone.
Figure 12:
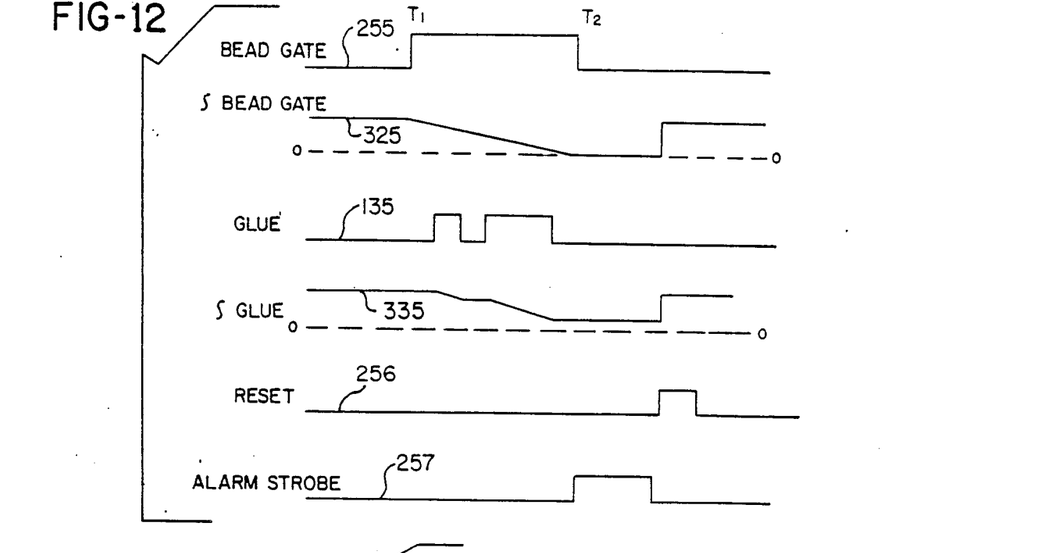
FIG. 12 is a waveform diagram showing the outputs at various points within the schematic of FIG. 11.

A portion of the circuit 230 is shown in FIG. 11, and the electrical signals at various locations within this circuit are represented in FIG. 12.

A bead gate signal on line 255 from the velocity and position circuit 250 is applied to a first integrator 320, and at time T1, the integrator voltage at the output line 325 begins to drop, as shown in FIG. 12.

A glue signal from circuit 200 on line 135 (see FIGS. 4 and 10) is applied to a second integrator 330, and its output on line 335 also changes as shown, but proportional to the amount of glue present. The two integrator outputs on lines 325 and 335 are compared by comparator circuit 340, and if at the end of the interval identified at T2 the volume of glue present is below an amount pre-set by potentiometer P1, then the comparator output, along with an alarm strobe signal on line 257 to the alarm indicator flip-flop 350 will provide an alarm output on line 235.

A reset signal resets the integrators to their initial values after the alarm signal is latched in the flip-flop 350 so that the circuit 230 is prepared to measure the volume of glue on the next board.

The circuit 230 also includes means for monitoring the glue output from all of the bead sensing and reference photodiodes to provide an alarm output if glue is found in zone C in the area before or after the desired area L2. This is done by using the bead gate signal 255 compared to the glue detected signals T1-T4 220 as shown in FIG. 14.

Figure 14:
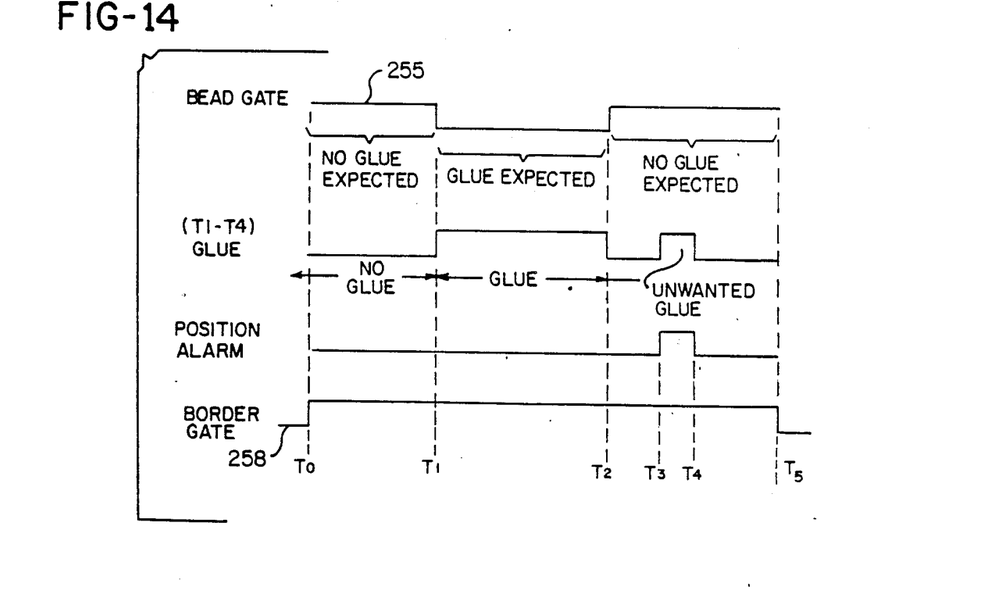
FIG. 14 is a timing diagram showing the signal produced by the velocity and position circuit and the sensor head.

In FIG. 14, the border gate waveform represents a signal that is initiated at time T0 upon the passage of the leading edge of the board under reference photocell R2. This signal is terminated at time T5 upon the passage of the trailing edge of the board past photodiode A1. It may be seen from FIG. 10 that both photodiodes A1 and R2 are connected through their respective amplifiers 300 and 304 to provide signals on lines EA1 and ER2 to the velocity and position circuit 250.

Figure 15:
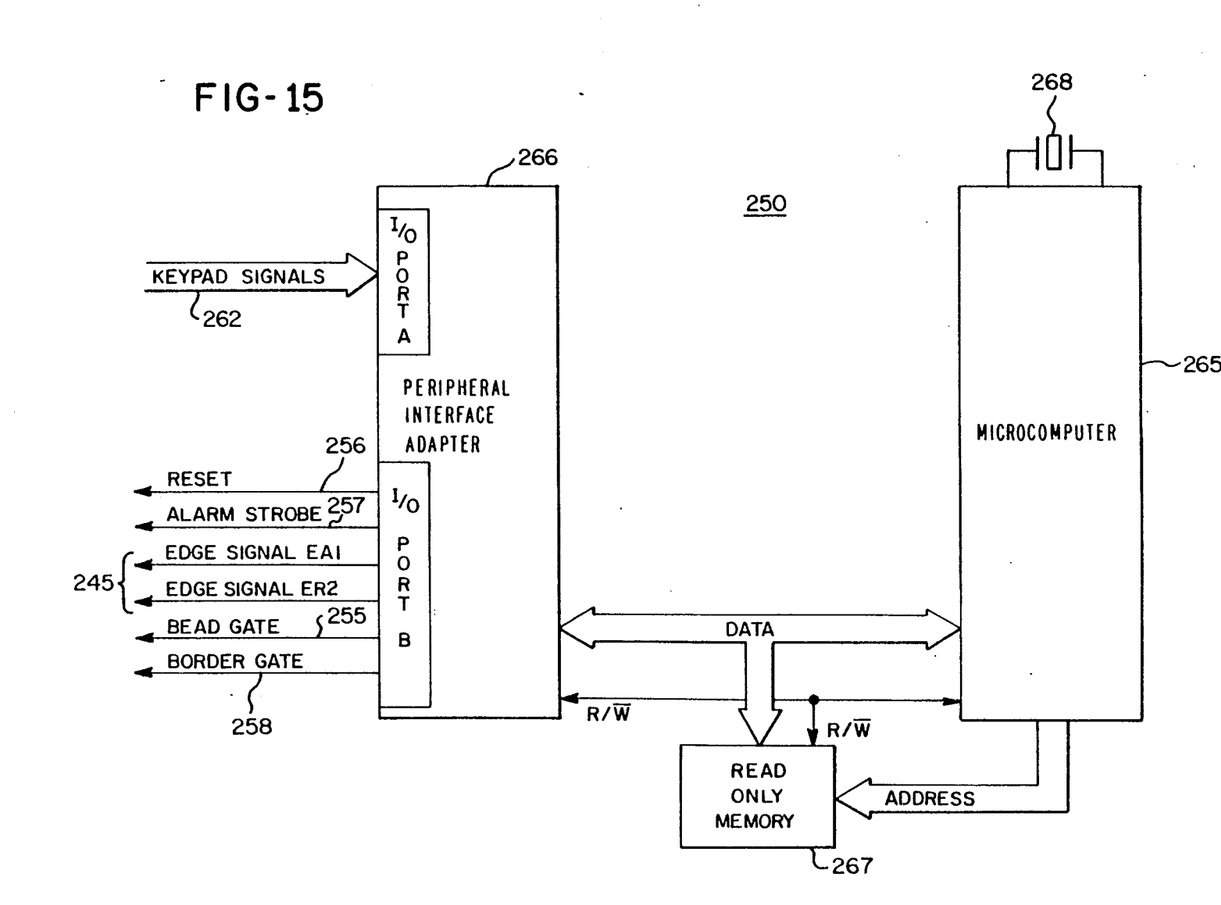
FIG. 15 is a block diagram of the velocity and position circuit.

The velocity and position circuit 250 includes a microcomputer 265, peripheral interface adapter 266, read-only memory 267, and a crystal time base 268, as shown in FIG. 15. The microcomputer is programmed to respond to keyboard signals and edge detector signal EA1 and ER2. The system operator enters the dimensions for L1 and L2 in FIG. 1 by means of the keyboard 260. These data are stored in the microcomputer memory and are used to determine the appropriate timing for the bead gate 255 and border gate 258 signals in FIG. 8.

With reference to FIG. 1, in order to relate the dimensions L1 and L2 to the gate signals, it is necessary to measure the velocity of the board 15 as it passes beneath the detector 30. This is achieved by an algorithm programmed in the microcomputer read-only memory. A memory location within the microcomputer is defined as a counter. This counter is cleared when no board is beneath the sensor assembly 30. The leading edge of the board passing beneath the sensor A1 in FIG. 2 causes signal EA1 to be generated. This change is detected by the microcomputer and the algorithm begins incrementing the counter at a predetermined fixed rate controlled by the crystal time base 268. The leading edge of the board passing beneath sensor R2 in FIG. 2 causes signal ER2 to be generated. The change in ER2 is sensed by the microcomputer and the incrementing of the counter ceases. The count now contained in the counter is directly proportional to the time required for the leading edge of the board to travel the known distance between sensors A1 and R2.

Thus, the distance D (FIG. 2) between photodiodes A1 and R2 is used by the circuit 250 to determine the velocity of the board as it passes beneath the detector 30, and the velocity of the board is equal to the distance D divided by the time it takes the leading edge of the board to move between the photodiodes A1 and R2. Alternatively, a tachogenerator associated with the board could be used to measure the movement of the board beneath the detector.

The time between T0 and T1, FIG. 14, is related to the distance L1 (FIG. 1) between the leading edge of the board and the location where the glue beads 25 are expected to begin. The interval T0 to T1 is therefore the length L1 divided by the velocity (L1/V). Similarly, the interval T1 to T2 is the distance L2 divided by the velocity (L2/V).

Thus, the signal on line 255 is a function of the information supplied by the operator and the actual velocity of the board.

The alarm strobe signal, shown in FIG. 12, is generated in the interval between T2 and T5. If, during this interval, unwanted glue is detected, such as at T3-T4, an alarm indication may be provided.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method for detecting the presence of substances on preselected areas of a surface comprising the steps of:
   positioning sensor photodetector means for observing light reflected from the surface in a preselected area intended to contain the substance;
   positioning reference photodetector means to observe other preselected areas which are intended to be free of the substance;
   providing light source means to illuminate the preselected areas whereby diffuse light reflected from the surface will be detected by each photodetector means in the absence of the substance and specular reflections will be observed when the substance is present in the field of view of either photodetector means;
   averaging the value of the light detected by the reference photodetector means;
   comparing the value of the light detected by said sensor photodetector means to said average value; and
   providing an output indicating the presence of the substance when the light value detected by the sensor photodetector means exceeds said average value by a predetermined amount.

2. Apparatus for determinign whether the surface of articles, such as blanks, have had glue properly applied thereto, said apparatus including:
   first detecting means for sensing the presence of glue within a predetermined band on each article;
   second detecting means for sensing the. presence of glue in a defined area adjacent said predetermined area;
   first circuit means responsive to said first detecting means for providing an output representing the presence of glue within said predetermined area;
   second circuit means responsive to said second detecting means for providing an output representing the presence of glue in said adjacent area; and
   alarm circuit means for providing an alarm signal indicating an improperlly glued surface whenever glue within said predetermined area deviates from a predetermined amount of whenever glue in excess of a second predetermined amount is present in said adjacent area.

3. Apparatus for determining the proper operation of a glue dispensing apparatus for applying glue onto one or more traces on a blank at specified locations, said apparatus including:
   detecting means for sensing the presence of the glue within each of the traces, said detecting means including,
      light source means for illuminating an area on the blank,
      sensor photodetector means for observing light reflected from the blank in an area including each trace, and
      reference photodetector means for observing light reflected from the surface of the blank adjacent to but not overlapping the area observed by the sensor photodetector means;
   circuit means responsive to said detecting means for providing an output representing specular reflections from each trace;
   means for sensing the movement of the blank past said detecting means; and
   alarm circuit means responsive to said movement sensing means and the output of said circuit means for providing an alarm signal whenever glue is detected prior to or after a predetermined location on the blank.

4. The apparatus of claim 3 wherein said alarm circuit means further provides an alarm signal whenever the amount of glue within the traces deviates from a predetermined amount.

5. The apparatus of claim 3 further including:
   second detecting means for sensing the presence of glue in a defined area adjacent the traces, said second detecting means including,
      light source means for illuminating said defined area;
      photodetector means for viewing the defined area; and
   second circuit means responsive to said second detecting means for providing an output representing specular light from the blank in the adjacent area; and
   wherein said alarm circuit means is also responsive to the output of said second circuit means for providing an alarm signal whenever glue is detected within the adjacent area.

6. The apparatus of claim 3 further including:
   means for sensing the length of each trace wherein specular reflections exceeding a predetermined value are detected.

7. The apparatus of claim 3 further including:
   means for sensing the volume of the glue present in each trace.

8. Apparatus for detecting substances on a surface of an article comprising:
   light source means for illuminating the surface;
   sensor photodetector means for observing light reflected from the surface in specifically designated areas;
   reference photodetector means for observing light reflected from the surface adjacent to but not overlapping the areas observed by sensor photodetector means; and
   circuit means fo comparing the average value of the output from said reference photodetector means and the output from said sensor photodetector means.

9. The apparatus of claim 8 wherein said light source means includes an incandescent lamp having a linear filament positioned parallel to the surface.

10. The apparatus of claim 8 wherein said sensor photodetector means includes photodiodes.

11. The apparatus of claim 8 wherein said photodetector means are positioned to view the surface normal thereto.

12. The apparatus of claim 8 wherein said light source means are so positioned with respect to the field of view of said photodetector means that specular light will not be observed by said photodetector means in the absence of a substance on the surface.

13. Apparatus for detecting substances on a surface of an article comprising:

light source means for illuminating an area on the surface;

a plurality of photodetector means for observing light reflected from the surface;

circuit means responsive to the outputs of said photodetector means for generating an average value thereof;

further circuit means, including a low pass filter, responsive to the output of said circuit means, for providing a filtered output of said average value; and comparator means for comparing the outputs of said circuit means and said further circuit means for providing an output indicating the presence of substances on the surface whenever there is a rapid change in the intensity of the light reflected from the surface.

* * * * *